United States Patent [19]

Franke et al.

[11] Patent Number: 4,743,622
[45] Date of Patent: May 10, 1988

[54] CERTAIN DIARYL-PENTANE DERIVATIVES HAVING PESTICIDAL PROPERTIES

[75] Inventors: Helga Franke; Heinrich Franke; Hans-Rudolf Krüger; Hartmut Joppien, all of Berlin, Fed. Rep. of Germany

[73] Assignee: Schering Aktiengesellschaft, Fed. Rep. of Germany

[21] Appl. No.: 828,289

[22] Filed: Feb. 11, 1986

[30] Foreign Application Priority Data

Feb. 14, 1985 [DE] Fed. Rep. of Germany ....... 3505370

[51] Int. Cl.⁴ ................. C07C 43/225; C07C 43/257; C07D 213/64; A01N 39/00
[52] U.S. Cl. .................... 514/717; 514/716; 514/718; 514/720; 514/721; 514/345; 514/347; 514/351; 514/277; 546/294; 546/300; 546/302; 546/329; 546/339; 558/58; 558/410; 568/637; 568/639; 568/644; 568/645
[58] Field of Search ............... 546/301, 329, 339, 346, 546/302, 294; 558/410, 58; 568/637, 639, 644, 645; 514/345, 351, 716, 717, 718, 721, 720

[56] References Cited

U.S. PATENT DOCUMENTS 4,570,005  2/1986  Nakatani et al. ................... 549/435

*Primary Examiner*—Alan L. Rotman
*Attorney, Agent, or Firm*—Ostrolenk, Faber, Gerb & Soffen

[57] ABSTRACT

The invention relates to new aromatic alkane derivatives of the general formula

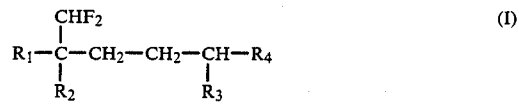
(I)

in which $R_1$ is aryl or aryl substituted by $C_{1-4}$ alkyl, halo-$C_{1-4}$ alkyl, phenyl-$C_{1-4}$ alkyl, $C_{2-4}$ alkenyl, halo-$C_{2-4}$ alkenyl, phenyl-$C_{2-4}$ alkenyl, $C_{2-4}$ alkynyl, halo-$C_{2-4}$ alkynyl, phenyl-$C_{2-4}$ alkynyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, alkylsulphonyloxy, haloalkylsulphonyloxy, arylsulphonyloxy, halo, cyano, nitro, aryloxy, haloaryloxy, $C_{1-4}$ alkyl-aryloxy, or nitroaryloxy, $R_2$ is hydrogen or $C_{1-4}$ alkyl, $R_3$ is hydrogen, cyano or ethynyl, $R_4$ is phenyl or pyridyl or these groups substituted by one or more of $C_{1-6}$ alkyl, halo-$C_{1-6}$ alkyl, phenyl-$C_{1-6}$ alkyl, $C_{1-6}$ alkyl interrupted by an O-, N- or S- atom, $C_{2-4}$ alkenyl, halo-$C_{2-4}$ alkenyl, phenyl-$C_{2-4}$ alkenyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, aryloxy, haloaryloxy, $C_{1-4}$ alkylaryloxy, arylamino, haloarylamino, $C_{1-4}$ alkylarylamino, aryl-N-$C_{1-4}$ alkylamino, aryl-N-$C_{1-4}$ acylamino, aroyl, haloaroyl, $C_{1-4}$ alkylaroyl, aryl, haloaryl, $C_{1-4}$ alkylaryl or halo, and pesticidal compositions containing these compounds as well as processes for their preparation.

11 Claims, No Drawings

CERTAIN DIARYL-PENTANE DERIVATIVES HAVING PESTICIDAL PROPERTIES

This invention relates to new aromatic alkane derivatives, compositions containing these compounds as well as processes for their preparation.

Compounds having similar activity are already known (DE-PS No. 1 493 646; DE-PS No. 1 076 662 and CH-PS No. 226 180).

The object of the present invention is the provision of new compounds that combat insect pests and mites, substantially better than compounds known for this purpose.

It has now been found that compounds of the general formula

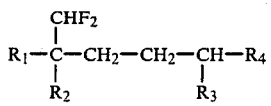  (I)

in which $R_1$ is aryl or aryl substituted by $C_{1-4}$ alkyl, halo-$C_{1-4}$ alkyl, phenyl-$C_{1-4}$ alkyl, $C_{2-4}$ alkenyl, halo-$C_{2-4}$ alkenyl, phenyl-$C_{2-4}$ alkenyl, $C_{2-4}$ alkynyl, halo-$C_{2-4}$ alkynyl, phenyl-$C_{2-4}$ alkynyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, alkylsulphonyloxy, haloalkylsulphonyloxy, arylsulphonyloxy, halo, cyano, nitro, aryloxy, haloaryloxy, $C_{1-4}$alkyl-aryloxy or nitroaryloxy, $R_2$ is hydrogen or $C_{1-4}$ alkyl, $R_3$ is hydrogen, cyano or ethynyl, $R_4$ is phenyl or pyridyl or these groups substituted by one or more of $C_{1-6}$ alkyl, halo-$C_{1-6}$ alkyl, phenyl-$C_{1-6}$ alkyl, $C_{1-6}$ alkyl interrupted by an O-, N- or S- atom, $C_{2-4}$ alkenyl, halo-$C_{2-4}$ alkenyl, phenyl-$C_{2-4}$ alkenyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, aryloxy, haloaryloxy, $C_{1-4}$ alkylaryloxy, arylamino, haloarylamino, $C_{1-4}$ alkylarylamino, aryl-N-$C_{1-4}$ alkylamino, aryl-N-$C_{1-4}$ acylamino, aroyl, haloaroyl, $C_{1-4}$ alkylaroyl, aryl, haloaryl, $C_{1-4}$ alkylaryl or halo, control insect pests and mites in a surprisingly better manner than known compounds of similar activity.

The aryl group designated as $R_1$ in general formula I also includes 1-naphthyl, 2-naphthyl, benzofuran-5-yl, benzothiophen-5-yl, benzofuran-6-yl, benzothiophen-6-yl, benzoxazol-5-yl, benzoxazol-6-yl, indan-5-yl, indan-6-yl, 1,4-benzodioxan-6-yl, 1,3-benzodioxan-6-yl, 1,3-benzodioxan-7-yl and 1,3-benzodioxol-5-yl.

Compounds of the invention showing particularly good activity are those in which in general formula I $R_1$ is chlorophenyl, bromophenyl, methylphenyl, methoxyphenyl, ethoxyphenyl, difluoromethoxyphenyl, fluoroethoxyphenyl, or trifluoroethoxyphenyl, $R_2$ is methyl, $R_3$ is hydrogen and $R_4$ is phenoxyphenyl, fluorophenoxyphenyl or phenoxypyridyl.

The compounds of the invention exist as optical isomers. Both the individual isomers and mixtures are within the scope of the invention.

The compounds according to the invention can be used at a concentration of 0.0005 to 5%, preferably from 0.001 to 1%.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example water, aliphatic and aromatic hydrocarbons, as well as cyclohexanone, isophorone, dimethylsulphoxide, dimethylformamide and mineral-oil fractions.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 5 to 95 percent by weight active ingredients, and about 95 to 5 percent by weight liquid or solid carriers, as well as, optionally up to 20 percent by weight of surfactant.

The agents can be applied in customary fashion, for example with water as the carrier in spray mixture volumes of approximately 100 to 3,000 l/ha. The agents can be applied using low-volume or ultra-low-volume techniques or in the form of so-called microgranules.

The preparation of these formulations can be carried out in a known manner, for example by milling or mixing processes. Optionally, individual components can be mixed just before use for example by the so-called commonly used tank-mixing method.

Formulations can be prepared, for example, from the following ingredients.

(A)

20 percent by weight active ingredient
35 percent by weight bentonite
8 percent by weight calcium lignosulphonate
2 percent by weight of the sodium salt of N-methyl-N-oleyltaurine
35 percent by weight silicic acid (B)

45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water (C)

20 percent by weight active ingredient
75 percent by weight isophorone
5 percent by weight of an emulsifier mixture of calcium phenylsulphonate and fatty alcohol polyglycol ether (D)

80 percent by weight active ingredient
15 percent by weight kaolin
5 percent by weight surface-active agent based on the sodium salt of N-methyl-N-oleyltaurine and the calcium lignosulphonate The compounds of the invention can be prepared by (a) reacting a compound of general formula $$R_5\overset{\oplus}{P}-CH_2CH_2R_4X^{\ominus} \quad (II)$$

or $$(R_6)_3\overset{O}{\overset{\|}{P}}-CH_2CH_2R_4 \quad (V)$$

first with a base and then with a compound of general formula $$R_1-\underset{R_2}{\overset{CHF_2}{\underset{|}{C}}}-CHO \quad (III)$$

to give a compound of general formula $$R_1-\underset{R_2}{\overset{CHF_2}{\underset{|}{C}}}-CH=CH-CH_2R_4 \quad (IV)$$

and reducing this to the desired product,
or (b) condensing a compound of general formula $$R_1-\underset{R_2}{\overset{CHF_2}{\underset{|}{C}}}-\underset{O}{\overset{\|}{C}}-CH_3 \quad (VI)$$

with an aldehyde of general formula $$R_4-CHO \quad (VII)$$

to give the $\alpha,\beta$- unsaturated carbonyl compound of general formula $$R_1-\underset{R_2}{\overset{CHF_2}{\underset{|}{C}}}-\underset{O}{\overset{\|}{C}}-CH=CH-R_4 \quad (VIII)$$

and reducing this to the desired product.
or (c) condensing a compound of general formula $$R_4-\overset{\|}{\underset{O}{C}}-CH_3 \quad (IX)$$

with an aldehyde of general formula $$R_1-\underset{R_2}{\overset{CHF_2}{\underset{|}{C}}}-CHO \quad (III)$$

to give the $\alpha,\beta$-unsaturated carbonyl compound of general formula $$R_1-\underset{R_2}{\overset{CHF_2}{\underset{|}{C}}}-CH=CH-\underset{O}{\overset{\|}{C}}-R_4 \quad (X)$$

and reducing this to the desired product, wherein $R_1$, $R_2$, $R_3$ and $R_4$ have the meanings given above, $R_5$ is an alkyl or phenyl group, $R_6$ is an alkyl group and X is a halogen atom.

The reaction variant (a) is carried out at a temperature of $-78°$ to $140°$ C., usually at atmospheric pressure and preferably in the presence of an inert solvent, such as those generally used in Wittig reactions. Suitable solvents include aliphatic or aromatic hydrocarbons, such as hexane, benzene or toluene, or ethers such as diethyl ether or tetrahydrofuran. If desired, further amides, such as dimethylformamide or hexamethylphosphoric acid triamide, as well as alcohols or dimethylsulphoxide can be used.

For the reaction variant (a) suitable bases include metal alcoholates such as for example sodium ethoxide, metal hydrides, such as for example sodium hydride, metal amides, such as for example sodamide, and organometallic compounds, such as for example phenyl lithium or butyl lithium.

Compounds of general formula I, in which $R_1$ is an alkoxy or haloalkoxy group etc., can be obtained by converting a hydroxyphenyl derivative, obtained by hydrolysis of another alkoxyphenyl derivative, using the corresponding halogenated compound.

The starting materials of general formula II or V for reaction variant (a) can easily be obtained by treatment of $R_4CH_2CH_2X$, wherein X is a halogen atom, with $(R_5)_3P$ or $(R_6O)_3$.

The aldehydes of general formula III used as starting materials can be prepared for example by reduction of the corresponding nitrile. The reduction can be carried out according to known methods with an alkyl aluminium hydride, such as for example diisobutyl aluminium hydride. The resulting nitrile can be converted to the corresponding arylnitrile with $CHClF_2$.

Compounds where $R_3$ is cyano, can be prepared from the corresponding starting compounds where $R_3$ is hydrogen, which are brominated with N-bromosuccinimide and the attached bromine is exchanged for cyano.

The following examples illustrate the preparation of compounds according to the invention.

EXAMPLE 1

2-(4-Ethoxyphenyl)-1,1-difluoro-5-(4-fluoro-3-phenoxyphenyl)-2-methylpentane 2.0 g (4.69 mmol) 4-(4-Ethoxyphenyl)-5,5-difluoro-1-(4-fluoro-3-phenoxyphenyl)-4-methyl-2-pentene was hydrogenated with hydrogen at atmospheric pressure with hydrogen in the presence of 0.2 g Raney nickel in 30 ml ethanol. After the calculated amount of hydrogen had been taken up, the catalyst was filtered off and the solvent removed under reduced pressure. After chromatography on silica gel, using hexane/toluene, 1.8 g of the desired product remained i.e. 89.6% of theory.

Refractive index $n_D^{20}$: 1.5481.

Analysis: Calculated: C 72.88%, H 6.35%, F 13.30%. Found: C 72.93%, H 6.31%, F 13.31%.

The starting and intermediate products were obtained as follows.

4-(4-Ethoxyphenyl)-5,5-difluoro-1-(4-fluoro-3-phenoxyphenyl)-4-methyl-2-pentene

To 6.38 g (11.4 mmol) of (2-(4-fluoro-3-phenoxyphenyl)ethyl)-4-triphenyl phosphonium bromide in 40 ml absolute alcohol was added dropwise at room temperature under a nitrogen atmosphere over 5 minutes 7.15 ml of 1.6 molar solution of butyl lithium in n-hexane. After stirring for an hour, a solution of 2.58 g (11.3 mmol) of 2-difluoromethyl-2-(4-ethoxyphenyl)propionaldehyde in absolute tetrahydrofuran was added dropwise. The mixture was stirred at room temperature for 18 hours. It was then added to ice water, extracted with ether, dried over sodium sulphate and evaporated. After silica gel chromatography using hexane/toluene, there remained 2.07 g of 4-(4-ethoxyphenyl)-5,5-difluoro-1-(4-fluoro-3-phenoxyphenyl)-4-methyl-2-pentene, i.e. 43% of theory.

Refractive index $n_D^{20}$: 1.5549.

2-difluoromethyl-2-(4-ethoxyphenyl)propionaldehyde

To 7.5 g (33.3 mmol) of 2-difluoromethyl-2-(4-ethoxyphenyl)propionitrile in 75 ml toluene was added dropwise with ice cooling and under a nitrogen atmosphere, 30.5 ml of a 1.2 molar solution of diisobutyl aluminium hydride in toluene. The mixture was then stirred at room temperature for 1.5 hours. It was then hydrolysed with 10% sulphuric acid, extracted with ethyl acetate, dried over sodium sulphate and the solvent removed under reduced pressure. There was thus obtained 6.47 g of the desired product as a light yellow oil, i.e. 93.1% of theory. TLC: Hexane/ether 1:1 RF=0.57.

EXAMPLE 1A 2-(4-Ethoxyphenyl)-1,1-difluoro-5-(4-fluoro-3-phenoxyphenyl)-2-methylpentane 1.5 g (3.75 mmol) 1,1-difluoro-5-(4-fluoro-3-phenoxyphenyl)-2-(4-hydroxyphenyl)-2-methylpentane, 10 ml dimethylformamide, 700 mg (4.5 mmol) ethyl iodide and 725 mg (5.25 mmol) $K_2CO_3$ were heated at 80° C. for 8 hours with a catalytic amount of sodium iodide. It was then added to water, extracted with ethyl acetate, dried over $Na_2SO_4$ and evaporated. After chromatography on silica gel, using hexane/toluene, 1.4 g of the desired product remained i.e. 87.4% of theory. The physical data are identical for the product of Example 1. The starting material was obtained as follows 1,1-Difluoro-5-(4-fluoro-3-phenoxyphenyl)-2-(4-hydroxyphenyl)-2-methylpentane 27.22 g (65.68 mmol) 1,1-Difluoro-5-(4-fluoro-3-phenoxyphenyl)-2-(4-methoxyphenyl)-2-methylpentane was heated with 75.92 g (657 mmol) pyridine hydrochloride at 180° C. for 7 hours. It was then added to water, extracted with ethyl acetate, and the organic phase washed until it was neutral, dried over $Na_2SO_4$ and evaporated. After chromatography on silica gel, using toluene/ethyl acetate, 24.5 g of the desired product remained i.e. 93.1% of theory. Refractive index $n_D^{20}$: 1.5571.

In a similar manner the following compounds according to the invention were prepared.

| Example No. | Compound | Physical constant $n_D^{20}$ |
|---|---|---|
| 2 | 2-(4-Chlorophenyl)-1,1-difluoro-2-methyl-5-(3-phenoxyphenyl)pentane | 1.5689 |
| 3 | 1,1-Difluoro-2-(4-methoxyphenyl)-2-methyl-5-(3-phenoxyphenyl)pentane | 1.5625 |
| 4 | 1,1-Difluoro-5-(4-fluoro-3-phenoxyphenyl)-2-methyl-2-(4-methylphenyl)pentane | 1.5498 |
| 5 | 1,1-Difluoro-2-methyl-2-(2-naphthyl)-5-(3-phenoxyphenyl)pentane | 1.5899 |
| 6 | 2-(4-Butoxyphenyl)-1,1-difluoro-2-methyl-5-(3-phenoxyphenyl)pentane | 1.5474 |
| 7 | 1,1-Difluoro-2-methyl-2-(4-n-propoxyphenyl)-5-(3-phenoxyphenyl)pentane | 1.5526 |
| 8 | 1,1-Difluoro-2-(4-isopropoxyphenyl)-2-methyl-5-(3-phenoxyphenyl)pentane | 1.5517 |
| 9 | 1,1-Difluoro-2-methyl-2-(4-methylsulphonyloxyphenyl)-5-(3-phenoxyphenyl)pentane | 1.5573 |
| 10 | 1,1-Difluoro-2-methyl-5-(3-phenoxyphenyl)-2-(4-trifluoromethylsulphonyloxyphenyl)pentane | 1.5230 |
| 11 | 1,1-Difluoro-2-methyl-5-(3-phenoxyphenyl)-2-[4-(2,2,2-trifluoroethoxy)phenyl]pentane | 1.5282 |
| 12 | 2-(4-Difluoromethoxyphenyl)-1,1-difluoro-2-methyl-5-(3-phenoxyphenyl)pentane | 1.5391 |
| 13 | 1,1-Difluoro-2-[4-(2-fluoroethoxy)phenyl]-2-methyl-5-(3-phenoxyphenyl)pentane | 1.5541 |
| 14 | 2-(4-Allyloxyphenyl)-1,1-difluoro-2-methyl-5-(3-phenoxyphenyl)pentane | 1.5612 |
| 15 | 1,1-Difluoro-2-methyl-5-(3-phenoxyphenyl)-2-(4-propargyloxyphenyl)pentane | 1.5643 |
| 16 | 2-(4-Tert.-butylphenyl)-1,1-difluoro-2-methyl-5-(3-phenoxyphenyl)pentane | 1.5502 |
| 17 | 2-(4-Chlorophenyl)-1,1-difluoro-2-methyl-5-(4-fluoro-3-phenoxyphenyl)pentane | |
| 18 | 1,1-Difluoro-5-(4-fluoro-3-phenoxyphenyl)-2-(4-methoxyphenyl)-2-methylpentane | 1.5530 |
| 19 | 2-(4-Butoxyphenyl)-1,1-difluoro-5-(4-fluoro-3-phenoxyphenyl)-2-methylpentane | 1.5414 |
| 20 | 1,1-Difluoro-5-(4-fluoro-3-phenoxyphenyl)-2-methyl-2-(4-n-propoxyphenyl)pentane | 1.5453 |
| 21 | 1,1-Difluoro-5-(4-fluoro-3-phenoxyphenyl)-2-(4-isopropoxyphenyl)-2-methylpentane | 1.5442 |
| 22 | 1,1-Difluoro-5-(4-fluoro-3-phenoxyphenyl)-2-methyl-2-(4-methylsulphonyloxyphenyl)pentane | 1.5501 |
| 23 | 1,1-Difluoro-5-(4-fluoro-3-phenoxyphenyl)-2-methyl-2-(4-trifluoromethylsulphonyloxyphenyl)pentane | 1.5172 |
| 24 | 1,1-Difluoro-5-(4-fluoro-3-phenoxyphenyl)-2-methyl-2-[4-(2,2,2-trifluoroethoxy)phenyl]pentane | 1.5240 |
| 25 | 2-(4-Difluoromethoxyphenyl)-1,1-difluoro-5-(4-fluoro-3-phenoxyphenyl)-2-methylpentane | 1.5323 |
| 26 | 1,1-Difluoro-2-[4-(2-fluoroethoxy)phenyl]-5-(4-fluoro-3-phenoxyphenyl)-2-methylpentane | 1.5469 |
| 27 | 2-(4-Allyloxyphenyl)-1,1-difluoro-2-methyl-5-(4-fluoro-3-phenoxyphenyl)pentane | 1.5540 |
| 28 | 1,1-Difluoro-5-(4-fluoro-3-phenoxyphenyl)-2-methyl-2-(4-propargyloxyphenyl)pentane | 1.5565 |
| 29 | 2-(4-Tert.-butylphenyl)-1,1-difluoro-5-(4-fluoro-3-phenoxyphenyl)-2-methylpentane | |
| 30 | 2-(4-Ethoxyphenyl)-1,1-difluoro-2-methyl-5-(6-phenoxy-2-pyridyl)pentane | |
| 31 | 2-(4-Chlorophenyl)-1,1-difluoro-2-methyl-5-(6-phenoxy-2-pyridyl)pentane | |
| 32 | 2-(4-Bromophenyl)-1,1-difluoro-5-(4-fluoro-3-phenoxyphenyl)-2-methylpentane | |
| 33 | 1,1-Difluoro-2-(4-fluorophenyl)-5-(4-fluoro-3-phenoxyphenyl)-2-methylpentane | 1.5638 |
| 34 | 2-(4-Ethoxyphenyl)-1,1-difluoro-2-methyl-5-(3-phenoxyphenyl)pentane | 1.5570 |
| 35 | 2-[4-(2,2-Dichlorovinyloxy)phenyl]-1,1-difluoro-5-(4-fluoro-3-phenoxyphenyl)- | 1.5638 |

-continued

| Example No. | Compound | Physical constant $n_D^{20}$ |
|---|---|---|
| | 2-methylpentane | |

The compounds are colourless and odourless oils that are highly soluble in most organic solvents but practically insoluble in water.

The following Examples illustrate the possible uses of the compounds of the invention, in the form that follows from the preparations.

EXAMPLE 36

Activity against larvae (L3) of the Mexican bean beetle (*Epilachna varivestis*)

Compounds of the invention were made up as aqueous emulsions at a concentration of 0.1%. French bean plants (*Phaseolus vulgaris*) in the primary leaf stage were dipped in the preparations. For each test two plant stems with 4 primary leaves were placed in glass vases filled with water and enclosed in glass cylinders. After drying off the preparation liquor, 5 larvae of the Mexican bean beetle (*Epilachna varivestis*) and the third larval stage were put in the glass cylinders and kept for 3 days. The % mortality of the larvae after 3 days indicated the level of activity.

It was found that the compounds of Examples 1–16, 18–28 and 33–35 caused 100% mortality at this concentration.

EXAMPLE 37

Activity against larvae of diamond-backed moth (*Plutella xylostella*)

The compounds of the invention as well as comparative substances were made up as aqueous emulsions at a concentration of 0.0025%. Cabbage leaves, placed in polystyrene petri dishes, were sprayed with these preparations (4 mg spray/cm²). After the sprayed surface had dried, 10 young larvae of the diamond-backed moth (*Plutella xylostella*) were placed in each petri dish and thereby exposed to the treated food in the closed dishes for two days. The % mortality of the larvae after two days indicated the level of activity. The results are summarised in the following table.

| Compounds of the invention | Concentration (%) | Activity (%) |
|---|---|---|
| 2-(4-Chlorophenyl)-1,1-difluoro-2-methyl-5-(3-phenoxyphenyl)pentane | 0.0025 | 100 |
| 2-(4-Ethoxyphenyl)-1,1-difluoro-5-(4-fluoro-3-phenoxyphenyl)-2-methylpentane | 0.0025 | 100 |
| 1,1-Difluoro-5-(4-fluoro-3-phenoxyphenyl)-2-methyl-2-(4-n-propoxyphenyl)pentane | 0.0025 | 60 |
| 1,1-Difluoro-5-(4-fluoro-3-phenoxyphenyl)-2-(4-isopropoxyphenyl)-2-methylpentane | 0.0025 | 85 |
| COMPARATIVE COMPOUND (according to DE-PS 149 36 46) 2,3-Dihydro-2,2-dimethylbenzofuran-7-yl methylcarbamate | 0.0025 | 20 |
| COMPARATIVE COMPOUND (according to DE-PS 107 66 62) O,O—Dimethyl-S—methylcarbamoylmethyl-phosphorodioate | 0.0025 | 0 |
| COMPARATIVE COMPOUND (according to CH-PS 226 180) 1,1,1-Trichloro-2,2-bis(4-methoxyphenyl)- | 0.0025 | 0 |

-continued

| Compounds of the invention | Concentration (%) | Activity (%) |
|---|---|---|
| ethane | | |

EXAMPLE 38

Activity against larvae (L2) of the cotton army worm (*Spodoptera littoralis*)

Compounds of the invention as well as a comparative compound were made up as aqueous emulsions at a concentration of 0.016%. Leaflet pairs of beans (*Vicia fabae*) as well as 10 larvae (L2) of the cotton army worm (*Spodoptera littoralis*) per experiment were sprayed with 4 mg spray/cm² of these preparations in polystyrene petri dishes. The closed petri dishes were left in the laboratory under extended daylight conditions for two days. The % mortality of the larvae after two days indicated the level of activity. Results are summarised in the following table.

| Compounds of the invention | Concentration (%) | Activity (%) |
|---|---|---|
| 1,1-Difluoro-5-(4-fluoro-3-phenoxyphenyl)-2-methyl-2-(4-methylphenyl)pentane | 0.016 | 100 |
| 1,1-Difluoro-2-(4-isopropoxyphenyl)-2-methyl-5-(3-phenoxyphenyl)pentane | 0.016 | 100 |
| 2-(4-Ethoxyphenyl)-1,1-difluoro-5-(4-fluoro-3-phenoxyphenyl)-2-methylpentane | 0.016 | 100 |
| 1,1-Difluoro-5-(4-fluoro-3-phenoxyphenyl)-2-methyl-2-(4-n-propoxyphenyl)pentane | 0.016 | 90 |
| 1,1-Difluoro-5-(4-fluoro-3-phenoxyphenyl)-2-(4-isopropoxyphenyl)-2-methylpentane | 0.016 | 100 |
| COMPARATIVE COMPOUND (according to DE-PS 149 36 46) 2,3-Dihydro-2,2-dimethylbenzofuran-7-yl methylcarbamate | 0.016 | 0 |
| COMPARATIVE COMPOUND (according to DE-PS 107 66 62) O,O—Dimethyl-S—methylcarbamoylmethyl-phosphorodioate | 0.016 | 0 |
| COMPARATIVE COMPOUND (according to CH-PS 226 180) 1,1,1-Trichloro-2,2-bis(4-methoxyphenyl)-ethane | 0.016 | 0 |

EXAMPLE 39

Activity against motile stages and eggs of the two spotted spider mite (*Tetranychus urticae*)

A selection of compounds of the invention were made up to an aqueous emulsion at a concentration of 0.1%. Dwarf bean plants (*Phaseolus vulgaris*) in the primary leaf stage, which had been infested with spider mites (*Tetranychus urticae*), were sprayed with these preparations until they were dripping wet and left in a laboratory for seven days. Thereafter, the % mortality of the motile stages on the one hand and the eggs on the other hand were estimated using a magnifying glass.

The results are shown in the following table.

| Compounds of Example No | Concentration (%) | Activity in % against *Tetranychus urticae* motile stages/eggs | |
|---|---|---|---|
| 2 | 0.1 | 100 | 20 |
| 1 | 0.1 | 100 | 0 |
| 7 | 0.1 | 100 | 0 |

-continued

| Compounds of Example No | Concentration (%) | Activity in % against Tetranychus urticae motile stages/eggs | |
|---|---|---|---|
| 8 | 0.1 | 100 | 0 |
| 10 | 0.1 | 100 | 50 |
| 11 | 0.1 | 100 | 20 |
| 12 | 0.1 | 100 | 0 |
| 19 | 0.1 | 100 | 0 |
| 20 | 0.1 | 100 | 100 |
| 27 | 0.1 | 100 | 80 |
| 28 | 0.1 | 100 | 0 |
| 22 | 0.1 | 100 | 0 |
| 26 | 0.1 | 100 | 50 |
| 24 | 0.1 | 100 | 100 |
| 25 | 0.1 | 100 | 70 |
| 23 | 0.1 | 100 | 100 |
| 33 | 0.1 | 100 | 100 |

EXAMPLE 40

Insecticidal and acaricidal activity against *Boophilus microplus* (1), *Lucilia sericata* (2) *Musca domestica* (3) and *Blattella germanica* (4).

1. 9 cm diameter filter papers were impregnated with 1 ml aliquots of acetone solutions of test compound at various concentrations. The papers were allowed to dry and then folded into envelopes in which cattle tick larvae (*Boophilus microplus*) were enclosed and held at 25° C. and 80% R.H. for 48 hours. The percentage mortality of tick larvae was then recorded and compared with controls.

The controls gave less than 5% reduction of reproductive capacity whereas compounds of Examples 1, 3, 6–8, 10–12, 14, 18–23, 25, 27, 28 and 34 had 90% mortality at a concentration of 100 ppm or less.

2. 1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blow fly (*Lucilia sericata*), closed by a cotton wool plug and held at 25° C. for 24 hours. For the controls the mortality was <5% whereas the compounds of Examples 1, 3–5, 10, 14–16, 18–25; 27, 28, and 34 had an $LC_{90}$ of 100 ppm or less.

3. Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies (*Musca domestica*) and held at 22° C. for 24 hours.

The percentage mortality of the insects was then recorded. Less than 5% mortality resulted in the control treatments whereas the compounds of Examples 1, 16, 20, 21, 23, 25 and 34 had an $LD_{90}$ of 100 mg/m² or less.

4. Aliquots of acetone solutions of test compounds at various concentrations were applied to glass plates (10 cm×10 cm). After evaporation of solvent, the treated surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the compounds of Examples 1, 6, 7, 10, 11, 12, 14, 16, 19, 20–25, 27, 28 and 34 had an $LD_{90}$ of 100 mg/m² or less.

We claim:

1. An aromatic alkane derivative of the formula

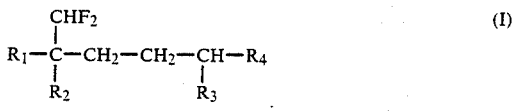

in which $R_1$ is phenyl or phenyl substituted by a member of the group consisting of $C_{1-4}$ alkyl, halo-$C_{1-4}$ alkyl, phenyl-$C_{1-4}$ alkyl, $C_{2-4}$ alkenyl, halo-$C_{2-4}$ alkenyl, phenyl-$C_{2-4}$ alkenyl, $C_{2-4}$ alkynyl, halo-$C_{2-4}$ alkynyl, phenyl-$C_{2-4}$ alkynyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{-2-4}$ alkynyloxy, methylsulfonyloxy, fluoromethylsulfonyloxy and halo, $R_2$ is hydrogen or $C_{1-4}$ alkyl, $R_3$ is hydrogen or ethynyl, and $R_4$ is phenyl or pyridyl or one of these groups substituted by one or more of $C_{1-6}$ alkyl, halo-$C_{1-6}$ alkyl, phenyl-$C_{1-6}$ alkyl, $C_{1-6}$ alkyl interrupted by an O-, N- or S- atom, $C_{2-4}$ alkenyl, halo-$C_{2-4}$ alkenyl, phenyl-$C_{2-4}$ alkenyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, phenoxy, halophenoxy or halo.

2. An aromatic alkane derivative of the formula

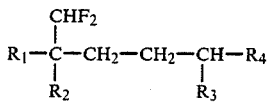

in which:

$R_1$ is chlorophenyl, bromophenyl, methylphenyl, methoxyphenyl, ethoxyphenyl, difluoromethoxyphenyl, fluoroethoxyphenyl, trifluoroethoxyphenyl or 4-trifluoromethylsulphonyloxyphenyl, $R_2$ is methyl, $R_3$ is hydrogen and $R_4$ is phenoxyphenyl, fluorophenoxyphenyl or phenoxypyridyl.

3. A pesticidal composition comprising an effective amount of a compound according to claim 1 in admixture with a diluent and/or a carrier.

4. Pesticidal composition according to claim 3 in which said compound is selected from the group consisting of 2-(4-ethoxyphenyl)-1,1-difluoro-5-(4-fluoro-3-phenoxyphenyl)-2-methylpentane; 1,1-difluoro-5-(4-fluoro-3-phenoxyphenyl)-2-methyl-2-(4-n-propoxyphenyl)pentane; 1,1-difluoro-5-(4-fluoro-3-phenoxyphenyl)-2-methyl-2-(4-trifluoromethylsulphonyloxyphenyl)pentane; and 2-(4-difluoromethoxyphenyl)-1,1-difluoro-5-(4-fluoro-3-phenoxyphenyl)-2-methylpentane.

5. Pesticidal composition according to claim 3 in which said compound is selected from the group consisting of 1,1-difluoro-2-methyl-2-(4-n-propoxyphenyl)-5-(3-phenoxyphenyl)pentane; 1,1-difluoro-2-methyl-5-(3-phenoxyphenyl)-2-(4-trifluoromethylsulphonyloxyphenyl)pentane; 1,1-difluoro-2-methyl-5-(3-phenoxyphenyl-2-[4-(2,2,2-trifluoroethoxy)phenyl]pentane; 2-(4-fluoromethoxyphenyl)-1,1-difluoro-2-methyl-5-(3-phenoxyphenyl)pentane; 2-(4-butoxyphenyl)-1,1-difluoro-5-(4-fluoro-3-phenoxyphenyl)-2-methylpentane; 1,1-difluoro-5-(4-fluoro-3-phenoxyphenyl)-2-(4-isopropoxyphenyl)-2-methylpentane; 1,1-difluoro-5-(4-fluoro-3-phenoxyphenyl)-2-methyl-2-(4-methylsulphonyloxyphenyl)pentane; 1,1-difluoro-5-(4-fluoro-3-phenoxyphenyl)-2-methyl-2-(4-propargyloxyphenyl)pentane; and 2-(4-ethoxyphenyl)-1,1-difluoro-2-methyl-5-(3-phenoxyphenyl)pentane.

6. An aromatic alkane derivative according to claim 1 selected from the group consisting of 2-(4-ethoxyphenyl)-1,1-difluoro-5-(4-fluoro-3-phenoxyphenyl)-2-methylpentane; 1,1-difluoro-5-(4-fluoro-3-phenoxyphenyl)-2-methyl-2-(4-n-propoxyphenyl)pentane; 1,1-difluoro-5-(4-fluoro-3-phenoxyphenyl)-2-methyl-2-(4-trifluoromethylsulphonyloxyphenyl)pentane; and 2-(4-difluoromethoxyphenyl)-1,1-difluoro-5-(4-fluoro-3-phenoxyphenyl)-2-methylpentane.

7. An aromatic alkane derivative according to claim 1 selected from the group consisting of 1,1-difluoro-2-methyl-2-(4-n-propoxyphenyl)-5-(3-phenoxyphenyl)pentane; 1,1-difluoro-2-methyl-5-(3-phenoxyphenyl)-2-(4-trifluoromethylsulphonyloxyphenyl)pentane; 1,1-difluoro-2-methyl-5-(3-phenoxyphenyl)-2-[4-(2,2,2-trifluoroethoxy)phenyl]pentane; 2-(4-difluoromethoxyphenyl)-1,1-difluoro-2-methyl-5-(3-phenoxyphenyl)pentane; 2-(4-butoxyphenyl)-1,1-difluoro-5-(4-fluoro-3-phenoxyphenyl)-2-methylpentane; 1,1-difluoro-5-(4-fluoro-3-phenoxyphenyl)-2-(4-isopropoxyphenyl)-2-methylpentane; 1,1-difluoro-5-(4-fluoro-3-phenoxyphenyl)-2-methyl-2-(4-methylsulphonyloxyphenyl)pentane; 1,1-difluoro-5-(4-fluoro-3-phenoxyphenyl)-2-methyl-2-(4-propargyloxyphenyl)pentane; and 2-(4-ethoxyphenyl)-1,1-difluoro-2-methyl-5-(3-phenoxyphenyl)pentane.

8. A method of controlling pests which comprises applying to the locus thereof, an effective pesticidal amount of an aromatic alkane derivative according to claim 1.

9. A method of controlling pests which comprises applying to the locus thereof, an effective pesticidal amount of an aromatic alkane derivative according to claim 2.

10. The method of claim 11 in which said compound is selected from the group consisting of 2-(4-ethoxyphenyl)-1,1-difluoro-(5-(4-fluoro-3-phenoxyphenyl)-2-methylpentane; 1,1-difluoro-5-(4-fluoro-3-phenoxyphenyl)-2-methyl-2-(4-n-propoxyphenyl)pentane; 1,1-difluoro-5-(4-fluoro-3-phenoxyphenyl)-2-methyl-2-(4-trifluoromethylsulphonyloxyphenyl)pentane; and 2-(4-difluoromethoxyphenyl)-1,1-difluoro-5-(4-fluoro-3-phenoxyphenyl)-2-methylpentane.

11. The method of claim 8 in which said compound is selected from the group consisting of 1,1-difluoro-2-methyl-2-(4-n-propoxyphenyl)-5-(3-phenoxyphenyl)pentane; 1,1-difluoro-2-methyl-5-(3-phenoxyphenyl)-2-(4-trifluoromethylsulphonyloxyphenyl)pentane; 1,1-difluoro-2-methyl-5-(3-phenoxyphenyl)-2-[4-(2,2,2-trifluoroethoxy)phenyl]pentane; 2-(4-difluoromethoxyphenyl)-1,1-difluoro-2-methyl-5-(3-phenoxyphenyl)pentane; 2-(4-butoxyphenyl)-1,1-difluoro-5-(4-fluoro-3-phenoxyphenyl)-2-methylpentane; 1,1-difluoro-5-(4-fluoro-3-phenoxyphenyl)-2-(4-isopropoxyphenyl)-2-methylpentane; 1,1-difluoro-5-(4-fluoro-3-phenoxyphenyl)-2-methyl-2-(4-methylsulphonyloxyphenyl)pentane; 1,1-difluoro-5-(4-fluoro-3-phenoxyphenyl)-2-methyl-2-(4-propargyloxyphenyl)pentane; and 2-(4-ethoxyphenyl)-1,1-difluoro-2-methyl-5-(3-phenoxyphenyl)pentane.

* * * * *